United States Patent [19]

Kang et al.

[11] 4,311,795
[45] Jan. 19, 1982

[54] POLYSACCHARIDE S-53 AND BACTERIAL FERMENTATION PROCESS FOR ITS PREPARATION

[75] Inventors: Kenneth S. Kang, LaJolla; George T. Veeder, San Diego, both of Calif.

[73] Assignee: Merck & Co., Inc., Rahway, N.J.

[21] Appl. No.: 210,115

[22] Filed: Nov. 24, 1980

Related U.S. Application Data

[62] Division of Ser. No. 16,253, Feb. 28, 1979.

[51] Int. Cl.³ ............................................. C12P 19/04
[52] U.S. Cl. ..................................... 435/101; 435/852
[58] Field of Search ....................... 435/101, 104, 852

[56] References Cited

U.S. PATENT DOCUMENTS 4,186,025  1/1980  Kang et al. ..................... 435/852 X
4,247,639  1/1981  Kang et al. ......................... 435/101

Primary Examiner—Thomas G. Wyse
Attorney, Agent, or Firm—Gabriel Lopez; Hesna J. Pfeiffer

[57] ABSTRACT

A novel polysaccharide S-53, having a composition of 18-19% uronic acid, 4.8% pyruvate, and 7% acetyl as the O-glycosidically linked ester; and the remainder neutral sugar, 51% glucose and 49% fucose. This polysaccharide is produced by the strain of *Klebsiella pneumoniae*, ATCC No. 31488 growing in a suitable fermentation medium.

2 Claims, No Drawings

POLYSACCHARIDE S-53 AND BACTERIAL FERMENTATION PROCESS FOR ITS PREPARATION

This is a division of application Ser. No. 16,253, filed Feb. 28, 1979.

BACKGROUND OF THE INVENTION

It is known that heteropolysaccharides can be produced by certain microorganisms. Some of such heteropolysaccharides function as hydrophilic colloids and because of their viscosity and rheology properties have been used as thickening agents for aqueous systems.

As with other fields of technology, research has continued with the objective of discovering new heteropolysaccharides having useful properties as thickening, suspending and/or stabilizing agents. It is an object of this invention to provide a new heteropolysaccharide having these desirable properties. It is another object to provide a method for making this new compound. A still further object is provision of formulations containing our new heteropolysaccharide as a thickening or suspending or stabilizing agent. Other objects of the invention will become evident from the ensuing description of this invention.

SUMMARY OF THE INVENTION

The present invention pertains to a novel heteropolysaccharide which is produced by the action of a bacterium on a selected carbon source. Further, the invention pertains to a novel process for producing a heteropolysaccharide by bacterial fermentation of a selected carbon source and fermentation medium ingredients under controlled conditions. The heteropolysaccharide of this invention is a high molecular weight polysaccharide containing primarily carbohydrate residues. It is sometimes referred to as a "gum" but it is believed that the heteropolycharide terminology is more accurate and precise. In the following description of our invention, it will sometimes be referred to as Heteropolysaccharide 53, or S-53.

This novel compound may be prepared by fermentation of a suitable nutrient medium with a novel strain of *Klebsiella pneumoniae*. An unrestricted permanent deposit of this organism employed in making our heteropolysaccharide was made with the American Type Culture Collection under Accession No. ATCC 31488.

Various classification keys for the genus Klebsiella and the culture descriptions of *Klebsiella pneumoniae* species and strains are found in the 7th Edition of Bergey's Manual (Breed et al., (1957)) and the 8th Edition of Bergey's Manual (Doudoroff et al., (1974).

A very similar polysaccharide is produced by another Klebsiella of very similar taxonomy, *Klebsiella pneumoniae*, type 1, see Erfing et al., Carbohydrate Research 50:115-120, 1976 "Structural Studies of the Capsular Polysaccharide From Klebsiella Type 1." The particular polysaccharide described therein contains no acetyl, while S-53 contains 7% acetyl.

FERMENTATION CONDITIONS:

The novel heteropolysaccharide S-53 is produced during the aerobic fermentation of suitable aqueous nutrient media under controlled conditions via the inoculation with the organism of the *Klebsiella pneumoniae* ATCC No. 31488. The media are usual media, containing source of carbon, nitrogen and inorganic salts.

In general, carbohydrates, for example, hydrolyzed starch, corn syrup of DE 24~42, glucose, fructose, maltose, sucrose, xylose, mannitol and the like can be used either alone or in combination as sources of assimilable carbon in the nutrient medium. The preferred carbon source is hydrolyzed starch. The hydrolyzed starch is prepared by reacting approximately 30% of starch which can be of different sources such as corn, tapioca, or potato, etc., with 1~2% of commercially available α-amylase at approximately 70°-80° C. for approximately 30 minutes. The exact quantity of the carbohydrate source or sources utilized in the medium depend in part upon the other ingredients of the medium but, in general, the amount of carbohydrate usually varies between about 2% and 4% by weight of the medium. These carbon sources can be used individually, or several such carbon sources may be combined in the medium. In general, many proteinaceous materials may be used as nitrogen sources in the fermentation process. Suitable nitrogen sources include, for example, soy peptone, yeast hydrolysates, primary yeast, soybean meal, cottonseed flour, hydrolysates of casein, corn steep liquor, distiller's solubles or tomato paste and the like. The sources of nitrogen, either alone or in combination, are used in amounts ranging from about 0.05% to 0.2% by weight of the aqueous medium.

Among the nutrient inorganic salts which can be incorporated in the culture media are the customary salts capable of yielding sodium, potassium, ammonium, calcium, phosphate, sulfate, chloride, carbonate, nitrate and like ions. A medium containing $NaNO_3$ definitely produces a higher yield than a medium to which $NaNO_3$ is not added. Also included are trace metals such as iron and magnesium.

It should be noted that the media described in the examples are merely illustrative of the wide variety of media which may be employed, and are not intended to be limitative.

The fermentation is carried out at temperatures ranging from about 25° C. to 35° C.; however, for optimum results it is preferable to conduct the fermentation at temperatures of from about 28° C. to 32° C. The pH of the nutrient media for growing the *Klebsiella pneumoniae* ATCC No. 31488 culture and producing the polysaccharide S-53 can vary from about 5.5 to 7.5.

Although the novel polysaccharide S-53 is produced by both surface and submerged culture, it is preferred to carry out the fermentation in the submerged state.

A small scale fermentation is conveniently carried out by inoculating a suitable nutrient medium with the culture and, after transfer to a production medium, permitting the fermentation to proceed at a constant temperature of about 30° C. on a shaker for from 1 day to several days.

The fermentation is initiated in a sterilized flask of medium via one or more stages of seed development. The nutrient medium for the seed stage may be any suitable combination of carbon and nitrogen sources. The seed flask is shaken in a constant temperature chamber at about 30° C. for 1-2 days, or until growth is satisfactory, and some of the resulting growth is used to inoculate either a second stage seed or the production medium. Intermediate stage seed flasks, when used, are developed in essentially the same manner; that is, part of the contents of the flask from the last seed stage are used to inoculate the production medium. The inoculated flasks are shaken at a constant temperature for several days, and at the end of the incubation period the contents of the flasks are recovered by precipitation with a suitable alcohol such as isopropanol.

For large scale work, it is preferable to conduct the fermentation in suitable tanks provided with an agitator and a means of aerating the fermentation medium. According to this method, the nutrient medium is made up in the tank and sterilized by heating at temperatures of up to about 121° C. Upon cooling, the sterilized medium is inoculated with a previously grown seed of the producing culture, and the fermentation is permitted to proceed for a period of time as, for example, from 2 to 4 days while agitating and/or aerating the nutrient medium and maintaining the temperature at about 30° C. This method of producing the S-53 is particularly suited for the preparation of large quantities.

The product is recovered from the fermentation medium by precipitation with a suitable alcohol, such as isopropanol.

Physical and Chemical Properties of the Polysaccharide S-53

The heteropolysaccharide produced by *Klebsiella pneumoniae* ATCC No. 31488 is composed of about 18-19% uronic acid, 4.8% pyruvate, 7% acetyl groups as the O-glycosidically linked ester and the remainder neutral sugar, 51% glucose and 49% fucose.

The acetyl content of 7% was determined by treating a 0.2% aqueous solution of S-53 gum with an alkaline, hydroxylamine reagent followed by treatment with an acidic ferric chloride reagent [S. Hestrin (1949) *J. Biol. Chem.* 180 249-261].

The neutral sugars of polysaccharide S-53 were determined by dissolving ten mg. of the product in 2 ml 2 N $H_2SO_4$, and the mixture is heated at 100° C. for 4 hours. The resulting solution is cooled, neutralized with barium hydroxide and the pH is brought to 5-6 with solid carbon dioxide. The resulting precipitate of barium sulfate is removed by centrifugation and the supernatent is concentrated to a syrup under reduced pressure. The sugars in the hydrolysate are tentatively identified by gas-liquid chromatography of their aldononitril acetate derivatives on a Hewlett-Packard Model 5750 chromatograph using 3% by weight OV-223 on 80/100 Gas Chrome Q at 210° C. The sugars are identified and quantitated by comparison with authentic standards [J. K. Baird, M. J. Holroyde, and D. C. Ellwood (1973) Carbohydr. Res. 27 464-467].

The various neutral sugars of the polysaccharides were also characterized by use of descending paper chromatography on Whatman No. 1 chromatography paper using as the solvent the upper layer of pyridine-:ethyl acetate:water (2:5:5). Chromatograms were stained using silver nitrate dip and acid analine phthalate spray reagent. Component sugars were identified by co-chromatography with sugar standards and by the specific-color reaction with the analine phthalate reagent.

An infrared spectrum of native S-53 was made on dried material in a KBr pellet. The heteropolysaccharide evidenced peaks at: 3400 cm$^{-1}$, 2950 cm$^{-1}$, 1720 cm$^{-1}$, and 1600 cm$^{-1}$ indicating hydroxyl groups, methylene groups, carboxyl groups, and carboxylic acid salts.

The polysaccharide S-53 imparts viscosity to an aqueous medium when dissolved in water in low concentrations. Because of this, its sensitivity to shear and overall rheology, its is useful as a thickening, suspending and stabilizing agent in aqueous systems; for example, as an additive to textile printing pastes or in formulating low drift aqueous herbicide compositions, salad dressings, thickened puddings, and adhesive compositions. It is particularly useful in thickening latex semi-gloss and flat paints, or in other paint applications.

The following detailed examples illustrate representative aspects of this invention.

EXAMPLE 1

Fermentation Procedure for the Isolation, Screening, General Fermentation Media, and Scale-Up Isolation The *K. pneumoniae* ATCC No. 31488 was isolated from a soil sample taken from the rhizosphere of *Gouania lupuloides* (a rapidly growing shrubby vine) at Summit, Canal Zone. The soil sample was moistened with sterile distilled water and stamped onto agar plates using a sterile polyurethane foam stamp. This strain was isolated from an agar plate which had been incubated at 30° C. for 48 hrs. and was composed of 0.5% $K_2HPO_4$, 0.01% $MgSO_4.7H_2O$, 0.05% Promosoy 10, 1% glucose, 0.09% $NH_4NO_3$ and 100 ppm methyl-green chloride. This strain was pure cultured on nutrient agar (Difco).

Screening

The heteropolysaccharide-producing S-53 was incubated (1 loopful) into 100 ml of YM (Difco) broth in a 500 ml Erlenmeyer flask and incubated at 30° C. on a rotary shaker (NBS) at 300-350 RPM for 24 hours. This seed was used to inoculate (1 ml) 40 ml. of a medium (3% hydrolyzed starch, 0.01% $MgSO_4$. $7H_2O$, 0.5% $K_2HPO_4$, 0.09% $NH_4NO_3$, 0.05% Promosoy 100, soy protein concentrate) in a 250 ml Erlenmeyer flask which was placed on a similar shaker at 30° C. and 350 RPM for 72 hrs. The fermentation liquor had a viscosity of 7400 cps (Brookfield Model LVF, 60 RPM, spindle No. 4), and a pH of 5.3. Upon the addition of 2-3 volumes of isopropyl alcohol, a fibrous precipitate formed which was collected and dried at 105° C. overnight. This yield weighed 0.519 gms.

Fermentation Improvement

Shake flask experiments were done in 500 ml unbaffled Erlenmeyer flasks. The flasks were incubated on a New Brunswick Model V gyrotary shaker until harvesting. The fermentation temperature was 30° C. The product was recovered by precipitation with 2-3 volumes of isopropyl alcohol, the fibers collected and dried at 55°-65° C. overnight. One-percent reconstituted viscosities are obtained by dissolving two grams of product in 198 grams of deionized water, using a Lightnin' mixer. Unless otherwise stated, all viscosities are measured using a Brookfield Model LVF viscometer with the appropriate spindle at 60 RPM.

The results in Table 1 demonstrate that this isolate produced a better fermentation in a medium containing $NaNO_3$. The carbon source was 3% hydrolyzed starch.

TABLE 1

| Medium Improvement of *K. pneumoniae* ATCC No. 31488 | | | |
|---|---|---|---|
| | Beer Vis. (cps) | Gum Yield (cps) | Product Vis. (cps) |
| Medium | | | |
| Standard medium from previous step | 19,200* | 1.66 | — |
| Standard + trace elements | 19,800* | 1.66 | — |
| Standard − $NH_4NO_3$ + 0.19% $NaNO_3$ | 100,000* | 1.71 | 1,650 |
| Standard − Promosoy 100 | 9,800 | 1.60 | — |
| Standard − Promosoy | | | |

TABLE 1-continued

Medium Improvement of *K. pneumoniae* ATCC No. 31488

| | Beer Vis. (cps) | Gum Yield (cps) | Product Vis. (cps) |
|---|---|---|---|
| + 0.025% Fish Peptone | 18,200* | 1.59 | — |
| Standard + 0.1% Promosoy | 20,000* | 1.72 | — |

*No. 4 spindle at 30 RPM
**No. 4 spindle at 6 RPM

Scale-Up

This isolate was scaled-up in a New Brunswick Scientific 70L fermentor with a working capacity of 50L. The medium consisted of 3% hydrolyzed starch, 0.19% $NaNO_3$, 0.01% $MgSO_4.7H_2O$, and 0.05% $K_2HPO_4$. A 5.6% inoculum from a 28-hr seed in a similar medium was used to start the fermentation. The pH was controlled at 6.0–7.0 through the addition of 25% KOH and an automatic pH control system. The aeration was set at 20L/min for the entire fermentation. Agitation was started at 300 RPM's and increased to 600 RPM at 33 hrs. The results of this scale up are shown in Table 2.

TABLE 2

Fermentation of S-53 Gum in 70L Fermentor

| Age | Beer Vis. (cps) | Gum Yield (gums/100 ml) | Residual Carbon Source | Product Vis. (cps) |
|---|---|---|---|---|
| 33.5 hrs | 5,950 | 1.36 | 0.80 | — |
| 60 hrs | 84,000* | 1.70 | 0.22 | 3,350 |

*No. 4 spindle at 6 RPM

EXAMPLE 2

Properties of the Heteropolysaccharide Gum S-53

Various standard tests were performed to determine the basic properties of the gum. These tests and results are summarized in tabular form below:

1. Viscosity and Shear

| A. | Brookfield | | | |
|---|---|---|---|---|
| 1. | 1.0% | | 60 RPM | 2150 cps |
| | | | 6 RPM | 11,000 cps |
| | | | Spindle No. 4 | |
| 2. | 0.1% | | (UL adapter)[a] | 34 cps |
| 3. | 0.5% | | Wells-Brookfield at 9.6 sec$^{-1}$ | 307 cps |
| B. | Shear[b] | | | |
| 1. | | | n at 1.92 sec$^{-1}$ | 4480 cps |
| 2. | | | n at 9.6 sec$^{-1}$ | 1984 cps |
| 3. | | | n at 76.8 sec$^{-1}$ | 320 cps |
| 4. | | | n at 384 sec$^{-1}$ | 64 cps |
| 5. | | | n at 384 sec$^{-1}$ | 64 cps |
| 6. | | | n at 9.6 sec$^{-1}$ | 1984 cps |

[a]Viscosity measured on a Brookfield Model LVF at 6 RPM with the No. 1 Spindle and a UL adapter.
[b]All measurements made on a Wells-Brookfield microviscometer Model RVT-c/p.

2. Acid, Base, Heat Stability

| A. | Stability | | |
|---|---|---|---|
| 1. | Acetic Acid plus heat | 99% | viscosity loss |
| 2. | 15% NaOH plus heat | Total % | viscosity loss[c] |
| 3. | Heat only | 79% | viscosity loss[c] |
| B. | pH Effect | | |
| 1. | 5% Acetic Acid | 3.0 pH | 1869 cps[c] |
| 2. | 5% $NH_4OH$ | 11.6 pH | 1331 cps[c] |

3. Salt and Dye Compatibility

| A. | Salt | |
|---|---|---|
| 1. | $CaCl_2$(saturated) | compatible |
| 2. | 1% $Al_2(SO_4)_3 \cdot 18H_2O$ | compatible |
| 3. | 1% $CaCl_2 \cdot 2H_2O$ | compatible |
| 4. | 1% KCl | compatible |
| 5. | 0.1% KCl | 844 cps[c] |
| 6. | 2.5% KCl | 1075 cps[c] |
| B. | Dyes | |
| 1. | Milling Green | compatible |
| 2. | Methylene Blue | precipitate |

4. Texture/Flow Properties:

Very smooth viscous flow; long, gummy to the touch; no gelation.

EXAMPLE 3

Uses for Heteropolysaccharide S-53

As noted above, S-53 is most useful in thickening latex paints, especially semi-gloss and flat. The gum can be added as a 2% aqueous solution to the latex paint formulation, or as a dry powder into the paint grind phase. The total amount of S-53 in the final paint formulation can be from 2-8 pounds per 100 gallons paint, and preferably 2.75-5 pounds per 100 gallons paint. At these levels, using paint formulations generally known in the art, good rheology control is achieved, coupled with good brushing or rolling properties, good scrub resistance, and good weatherability.

Other applications for S-53 include as a rheology modifier in textile and carpet printing, in oil well drilling, and water flooding for secondary oil recovery, and as a thickener and stabilizer in drywall joint paste.

What is claimed is:

1. A process for producing a heteropolysaccharide S-53 comprising incubating in a fermentation medium containing a carbon source, a source of potassium ions, a source of nitrogen, preferably including soy peptone; trace inorganic elements and water, the *Klebsiella pneumoniae* organism, ATCC 31488, at a temperature of 30° C. and pH of 6.5 for 50 hours, and recovering the gum by precipitation with a suitable lower alcohol, such as isopropanol.

2. The process of claim 1 in which $NaNo_3$ is added in a proper amount to the fermentation medium.

* * * * *